United States Patent
Beck et al.

(10) Patent No.: US 9,870,447 B2
(45) Date of Patent: Jan. 16, 2018

(54) MEDICAL DATA TRANSFER COMPONENT

(71) Applicant: Roche Diagnostics Operations, Inc., Indianapolis, IN (US)

(72) Inventors: Timothy L. Beck, Pendleton, IN (US); Daniel Birtwhistle, Fishers, IN (US); Samer M. Dajani, Carmel, IN (US); Jonathon Fuller, Noblesville, IN (US); Igor Gejdos, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 65 days.

(21) Appl. No.: 14/172,261

(22) Filed: Feb. 4, 2014

(65) Prior Publication Data
US 2014/0324462 A1     Oct. 30, 2014

Related U.S. Application Data

(60) Provisional application No. 61/816,235, filed on Apr. 26, 2013.

(51) Int. Cl.
*G06F 19/00*     (2011.01)

(52) U.S. Cl.
CPC .......... *G06F 19/323* (2013.01); *G06F 19/322* (2013.01); *G06F 19/3406* (2013.01); *G06F 19/3412* (2013.01); *G06F 19/3418* (2013.01)

(58) Field of Classification Search
CPC ...... G06Q 50/22; G06Q 50/24; G06F 19/322; G06F 19/3406; G06F 19/3418
USPC .................................................. 705/2, 3, 4
See application file for complete search history.

(56) References Cited

U.S. PATENT DOCUMENTS

| | | |
|---|---|---|
| 6,368,273 B1 | 4/2002 | Brown |
| 6,442,432 B2 | 8/2002 | Lee |
| 6,589,169 B1 | 7/2003 | Surwit et al. |
| 7,103,578 B2 | 9/2006 | Beck et al. |
| 7,188,151 B2 | 3/2007 | Kumar et al. |
| 7,463,930 B2 | 12/2008 | Housworth et al. |
| 8,615,532 B2 | 12/2013 | Bessette |

(Continued)

FOREIGN PATENT DOCUMENTS

| | | | |
|---|---|---|---|
| ES | WO-2006108858 A1 * | 10/2006 | ............... G06F 8/60 |
| WO | 02/15530 A2 | 2/2002 | |

(Continued)

OTHER PUBLICATIONS

Harrison, Ann, "Tokens: Not Just for Security Anymore; Merged hospitals use tokens for single point of security and clinical data," Mar. 22, 1999, Computerworld 64(1).*

(Continued)

*Primary Examiner* — Sean K. Hunter
*Assistant Examiner* — John P Go
(74) *Attorney, Agent, or Firm* — Harness Dickey (57) ABSTRACT

Diabetes care management system and method for transferring medical data from a handheld medical recording device to a host computer via a data transfer component. The steps of the data transfer component comprising detecting a data upload request and detecting a medical device ready to communicate, verifying a unique ID, receiving patient medical data, including an authentication token with patient medical data, and sending patient medical data along with the authentication token for association with a user account.

11 Claims, 7 Drawing Sheets

(56) References Cited

U.S. PATENT DOCUMENTS

| | | |
|---|---|---|
| 2002/0016718 A1 | 2/2002 | Rothschild et al. |
| 2002/0016721 A1 | 2/2002 | Mason et al. |
| 2003/0216624 A1* | 11/2003 | Lin .................... A61B 5/0002 600/300 |
| 2003/0217159 A1 | 11/2003 | Schramm-Apple et al. |
| 2004/0111297 A1* | 6/2004 | Schoenberg .......... G06Q 10/10 705/3 |
| 2004/0167465 A1 | 8/2004 | Mihai et al. |
| 2005/0267780 A1* | 12/2005 | Ray .................... G06F 19/3406 705/2 |
| 2006/0036555 A1 | 2/2006 | Beck et al. |
| 2006/0184524 A1 | 8/2006 | Pollanz |
| 2007/0088521 A1* | 4/2007 | Shmueli ............... A61B 5/0205 702/127 |
| 2007/0282175 A1* | 12/2007 | Urbaszek ............. A61B 5/0031 600/300 |
| 2008/0004904 A1 | 1/2008 | Tran |
| 2008/0101597 A1 | 5/2008 | Nolan et al. |
| 2008/0140162 A1 | 6/2008 | Goetz et al. |
| 2008/0154099 A1 | 6/2008 | Aspel et al. |
| 2009/0099864 A1* | 4/2009 | Cronrath ................. G06F 8/60 705/2 |
| 2010/0240982 A1* | 9/2010 | Westbrook ............ A61B 5/087 600/391 |
| 2010/0292556 A1 | 11/2010 | Golden |
| 2010/0324934 A1 | 12/2010 | Selinfreund et al. |
| 2011/0119080 A1* | 5/2011 | Hayter ............... A61B 5/14532 705/2 |
| 2011/0191822 A1 | 8/2011 | Pinsky et al. |
| 2012/0232367 A1* | 9/2012 | Allegri .................. A61B 5/145 600/365 |
| 2012/0266251 A1 | 10/2012 | Birtwhistle et al. |
| 2013/0036412 A1 | 2/2013 | Birtwhistle et al. |
| 2013/0229288 A1 | 9/2013 | Alexander et al. |

FOREIGN PATENT DOCUMENTS

| | | |
|---|---|---|
| WO | 03/053123 A2 | 7/2003 |
| WO | WO-2004070546 A2 | 8/2004 |

OTHER PUBLICATIONS

Kohl, J., "RFC 1510—The Kerberos Network Authentication Service (V5)", Network working group request for comments, Digital Equipment Corporation, Sep. 1993, 70 pages, XP002254582.

"Software token", Wikipedia, the free encyclopedia, 2012, XP055150633, http://en.wikipedia.org/w/index.php?title=Software_token&oldid=509808418.

"Authentication", Wikipedia, the free encyclopedia, 2012, XP055151742, http://en.wikipedia.org/w/index.php?title=Authentication&oldid=548140433.

* cited by examiner

MEDICAL DATA TRANSFER COMPONENT

CROSS-REFERENCE TO RELATED APPLICATIONS

This application claims the benefit of U.S. Provisional Application No. 61/816,235, filed on Apr. 26, 2013. The entire disclosure of the above application is incorporated herein by reference.

FIELD

The present disclosure relates to diabetes care management systems and methods that support transfer of medical data from a handheld medical device to a host computer.

BACKGROUND

Patients with diabetes rely on handheld medical recording devices to measure and document their blood glucose level. Patients may need to take several measurements throughout the day, including before and after meals. The measured blood glucose level may determine amount of insulin the patient will need to bring it to a desired blood glucose level. Following an insulin injection, diabetes patients may need to measure their blood glucose level once more to confirm the injection had the desired effect on their blood sugar level.

Medical specialist may analyze the reported blood glucose levels for a given patient to monitor the progress patient makes in stabilizing their blood glucose level through the use of insulin, appropriate diet, and regular exercise. How successful the patient is in managing their blood sugar may determine how the medical specialist will advise them during the following visit to the specialist's office. Monitoring blood glucose level over a significant period of time may allow patient and medical specialist to apply a multitude of strategies in achieving the desired blood sugar level for the patient.

Patient medical data may be transferred from the handheld medical device to a medical specialist's patient database for their review and analysis. A variety of ways exist to transfer medical data from a handheld medical device to the medical specialist's database. Connecting the handheld medical recording device to the Internet is an expedient way of transferring patient medical data from the medical device to the specialist's database. The need exists for such medical data transfer system and method to be highly secure, resistant to brute-force and sniffing attacks, in order to preserve the privacy of the patient and the integrity of patient medical data.

This section provides background information related to the present disclosure which is not necessarily prior art.

SUMMARY

This section provides a general summary of the disclosure, and is not a comprehensive disclosure of its full scope or all of its features.

A computer-implemented method for transferring medical data from a handheld medical recording device to a host computer including accessing an account using a web browser on a patient computer, where the account resides on the host computer and is associated with a patient, downloading a device transfer component from the host computer via network to the patient computer, establishing, by the device transfer component, an association between the patient account and the device transfer component at the host computer, receiving, by the device transfer component, an authentication token from the host computer, receiving, by the device transfer component, medical data from a handheld medical device being associated with the patient, sending, by the device transfer component, the medical data, along with the authentication token, over the network to the host computer, and associating, at the host computer, the medical data with the patient account, where the association is made using the authentication token received with the medical data.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
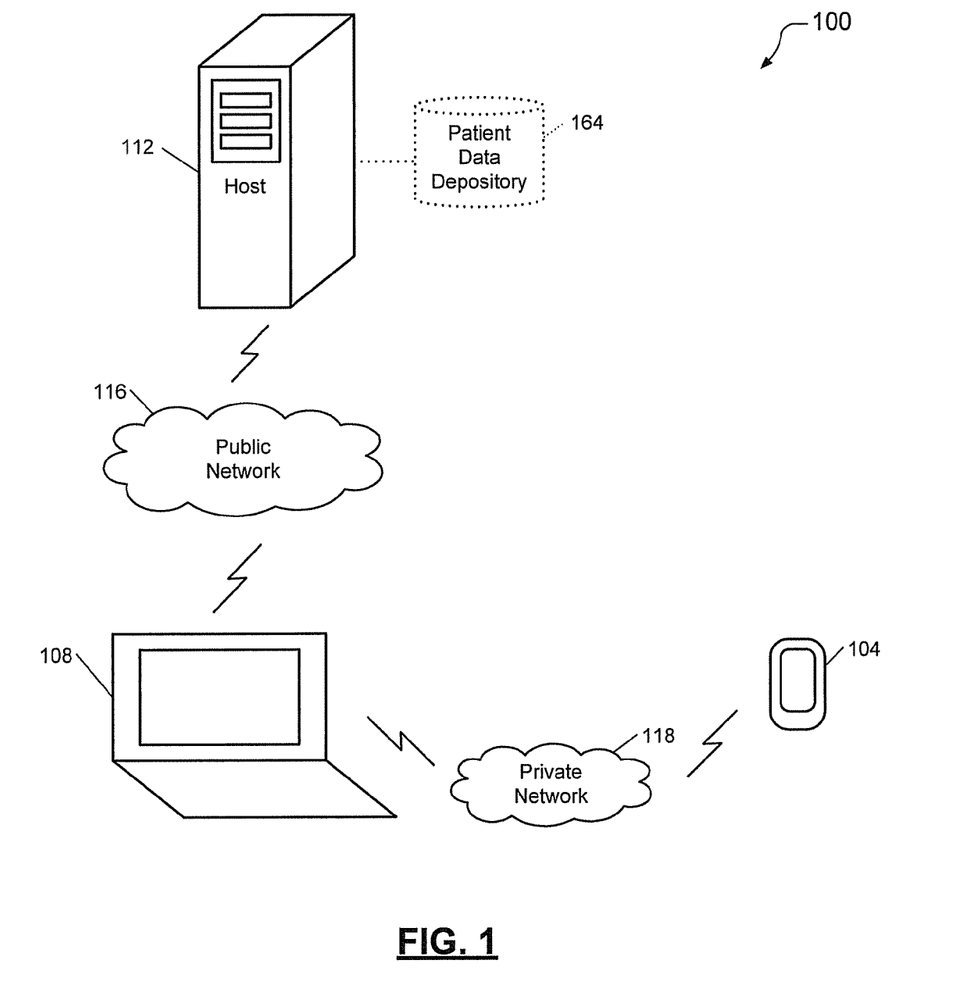
FIG. 1 is a functional block diagram of an example implementation of computer-implemented method for transferring medical data.

In FIG. 1 a medical data transfer system 100 generally comprises a handheld medical recording device (hereinafter, medical device) 104, a patient computer 108, and a host computer 112. The medical device 104 is used to capture patient medical data, e.g., blood glucose measurements, and is connectable to the patient computer 108 for transmission of the captured data to the host computer 112 via a public network 116. In an example embodiment, the medical device 104 connects to the patient computer 108 in order to transmit patient medical data to the host computer 112 and to accept data transfers from the host computer 112. The host computer 112 includes a patient data depository 164 for hosting patient medical data in order to enable access by the patient and/or by medical specialists caring for the patient. In an example embodiment, the patient data depository 164 is a database, e.g., cloud database.

Each of the patient computer 108 and the host computer 112 connect to the public network 116 to facilitate patient medical data transfers. In an example embodiment, each of the patient computer 108 and the host computer 112 include a communication module for communicating with the public network 116. In an example embodiment, the communication module includes a wired communication channel such as Ethernet or a wireless communication channel such as the cellular network. In the example embodiment, the communication module includes other communication channels for electronically communicating with the public network 116. The public network 116 includes the Internet.

The medical device 104 is connected to a private network 118 and transmits patient medical data to the patient computer 108 through the private network 118, for example the private network in the patient's home. In an example embodiment, the medical device 104 is directly connected to the private network 118. In another example embodiment, the medical device 104 connects to the private network 118 through a wired connection, such as Universal Serial Bus (USB), RS-232, or the like, or through wireless communications, such as the Bluetooth, Infra-Red (IR), or the like.

The patient computer 108 includes a processor, a memory, an input device and an output device. The processor is connected to the memory, the input device and the output device. In an example embodiment, the processor includes a general purpose processor. In another example embodiment, the processor includes an application specific integrated circuit. The input device includes a keyboard, a mouse, a touchpad, a trackpad, or the like. The output device includes a display, a speaker, or the like. The patient computer 108 includes a desktop computer located in the patient's home. In an example embodiment, the patient computer 108 includes a laptop computer, or a mobile communication device such as an electronic tablet or a smart phone.

To enable initial transfer of patient medical data to the patient data depository 164 the patient may need to setup a user account using personal credentials, e.g., first and last name, date of birth, address, and name of medical specialist caring for them. In an example embodiment, the patient sets up the user account with the patient data depository 164 through a web-based user interface via the patient computer 108 connected to the public network 116. As part of the user account setup process the web-based user interface may prompt the patient to create login credentials to access the user account in the future. The host computer 112 associates patient medical data transfers to the patient data depository 164 with the user account the patient created.

Medical specialists access the patient data depository 164 by using a medical specialist device. The medical specialist device includes a desktop computer located in the medical specialist's office. In an example embodiment, the medical specialist device includes a laptop computer, or a mobile communication device such as an electronic tablet or a smart phone. The medical specialist device is connected to the public network 116 and accesses the patient data depository 164 through the public network 116. In an example embodiment, the medical specialist device is directly connected to the public network 116. In another example embodiment, the medical specialist device is connected to the public network 116 through a private network, for example the private network in the physician's office. In another example embodiment, the medical specialist device connects to the public network 116 through a wired connection such as Ethernet or through wireless communications such as the cellular network, Wireless Local Area Network (WLAN), Bluetooth or the like.

Access to the patient data depository 164 may be restricted and the medical specialist device may prompt the medical specialist to provide login credentials to access the patient medical data. In an example embodiment, the medical specialist device accesses the patient data depository 164 through a web-based user interface over the public network 116. In the example embodiment, a medical specialist is a physician. The medical specialist can also include a nurse, an assistant to the physician, a medical resident, a medical student, or the like.

Figure 2A:
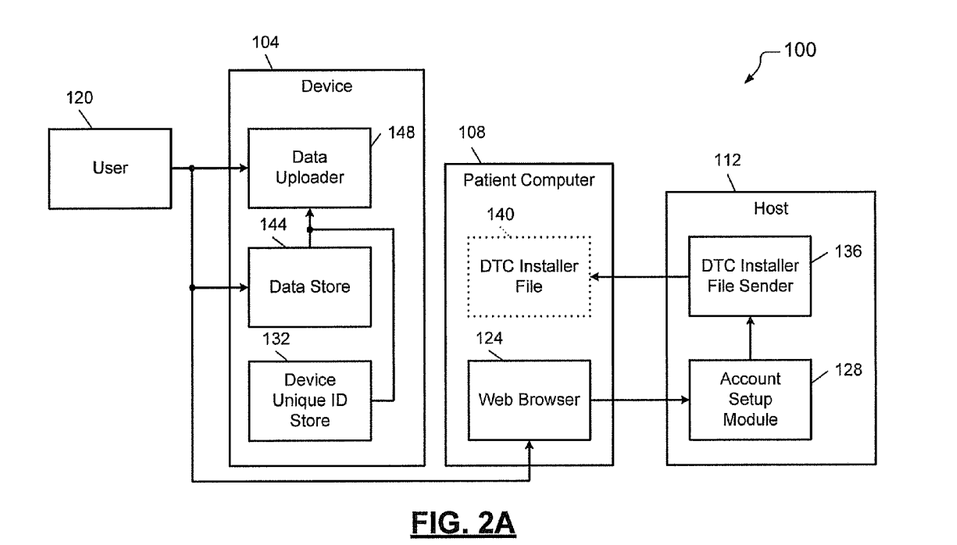
FIGS. 2A-2C are functional block diagrams of an example implementation of computer-implemented method for transferring medical data.
Figure 2B:
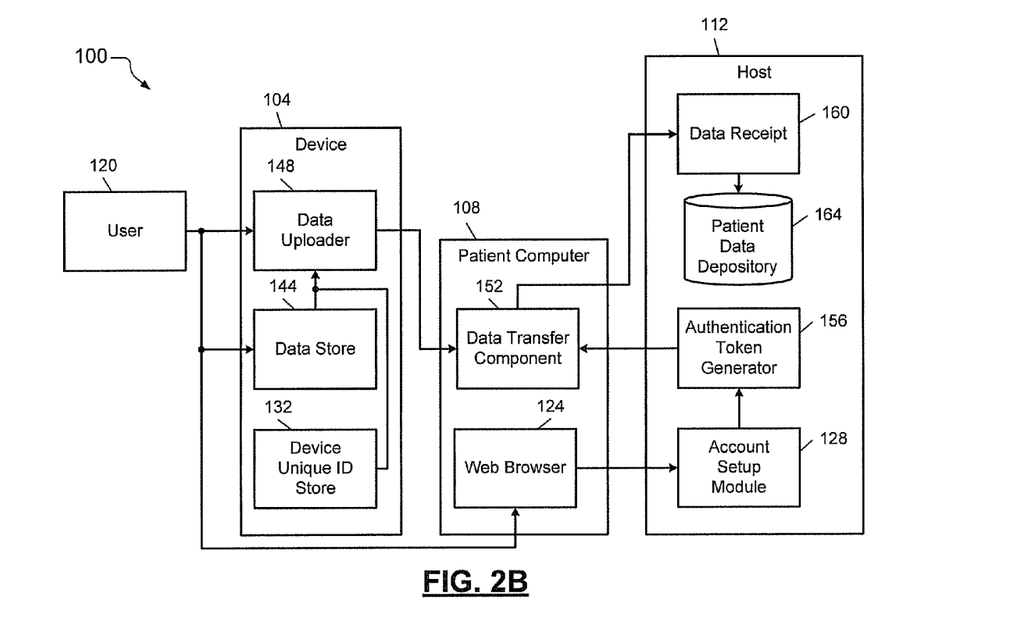
Figure 2C:
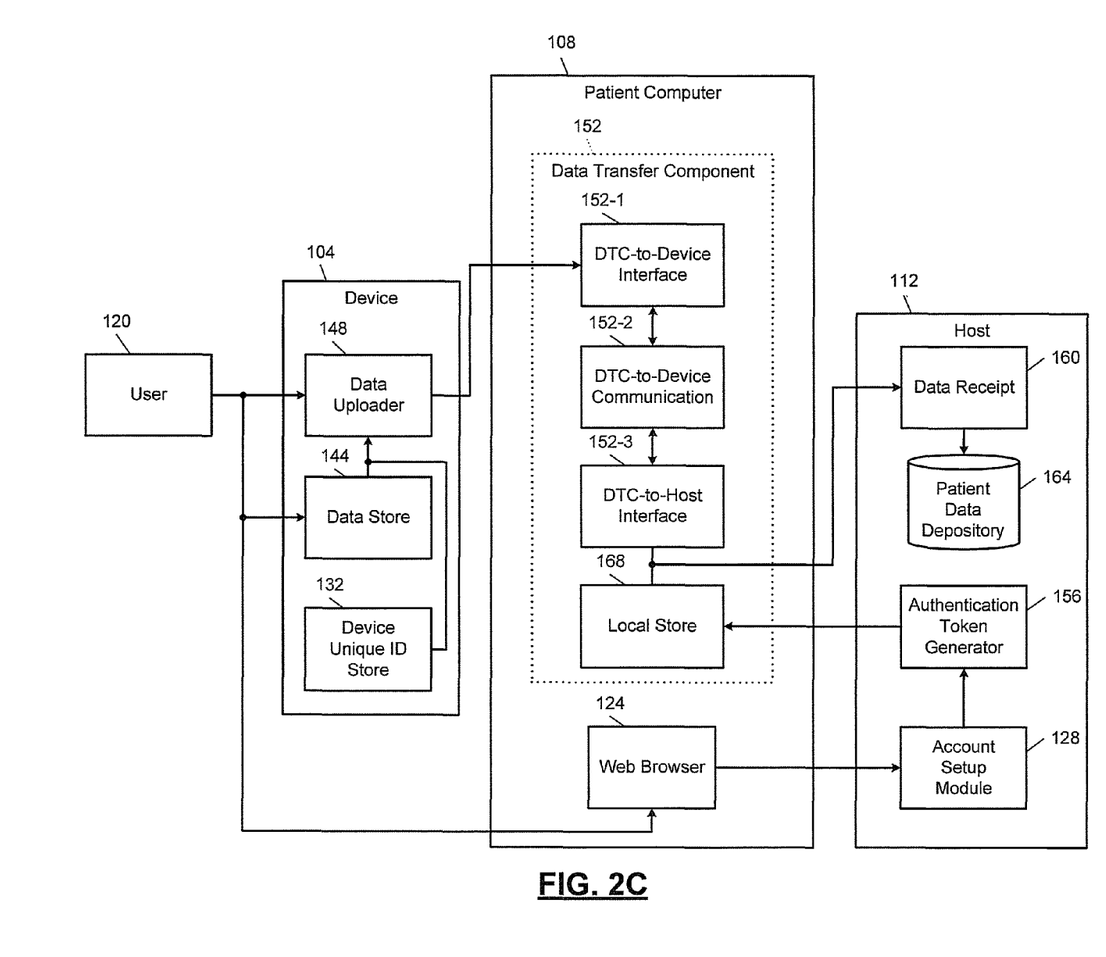

FIGS. 2A-2C illustrate the medical data transfer system 100 in further detail. Referring to FIG. 2A, the medical device 104 includes a device unique ID store 132, a data uploader 148, and a data store 144. In an example embodiment, each of the device unique ID store 132 and the data store 144 is a cache or a memory of the medical device 104. The device unique ID store 132 stores a unique ID, e.g., serial number, model unique ID, device type, and/or model name, of the medical device 104. The data store 144 stores medical data that a user 120 captures using the medical device 104, e.g., blood glucose measurements. As will be discussed below in further detail, the data uploader 148 uploads the unique ID from the device unique ID store 132 to the patient computer 108. As will be further discussed below, the data uploader 148 uploads patient medical data from the data store 144 to the patient computer 108.

The patient computer 108 includes a web browser 124, a web-based user interface for access to the public network 116, such as the Internet. The host computer 112 includes an account setup module 128 that manages a patient account setup process and a DTC installer file sender 136.

In an example embodiment, a user 120, e.g., a diabetes patient, accesses a patient data management website via the web browser 124 on the patient computer 108 and initiates the patient account setup process. During the patient account setup process the account setup module 128 may ask the user 120 to enter personal information, including, first and last name, date of birth, address, and name of the medical specialist caring for the patient. The account setup module 128 may ask the user 120 to create login credentials, e.g., user ID and password, for secure access to their account in the future. In an alternative embodiment, the patient account setup process may be completed in a different way. In another embodiment, the user account may already exist and does not need to be set up.

The DTC installer file sender 136 of the host computer 112 downloads a DTC installer file 140 onto the patient computer 108 following completion of the patient account setup process. In an example embodiment, the user 120 prompts the DTC installer file sender 136 to download the DTC installer file 140 onto the patient computer 108 by selecting "Download DTC Installer File" on the patient data management website. In the example embodiment, the DTC installer file 140 is an executable file of encoded, e.g., machine code, instructions for the processing unit of the patient computer 108. In an example embodiment, the DTC installer file 140 instructs the processor of the patient computer 108 to install a data transfer component 152, as shown in FIG. 2B.

Following installation of the data transfer component 152 on the patient computer 108, the host computer 112 may require further steps to complete a device-to-account association process. In an example embodiment, the user 120 launches the data transfer component 152 for the first time and is prompted to enter their patient account login credentials. The data transfer component 152 may then capture the unique ID of the medical device 104. In an example embodiment, the data transfer component 152 receives the unique ID from the data uploader 148 of the medical device 104 and transfers it to the host computer 112. As will be described further below, the host computer 112 associates the unique ID with the user account. Other methods of receiving and associating the unique ID are also contemplated. In an example embodiment, the user 120 is not required to enter login credentials following completion of the device-to-account association process. In the example embodiment, the data transfer component 152 transfers data without requiring the user 120 to enter their login credentials following completion of the device-to-account association process. In an alternative embodiment, the user 120 enters login credentials following completion of the device-to-account association process. In the alternative embodiment, the data transfer component 152 transfers data to the host computer 112 after the user 120 enters login credentials.

Along with the unique ID, the data transfer component 152 may also transfer a medical device name, e.g., a friendly name, which the user 120 assigned to the medical device 104 using the patient data management website. Other methods of assigning the medical device name by the user 120 are also contemplated. In an example embodiment, the medical device name, e.g., "Dale's Meter", "Abbey's Pump", helps the user 120 quickly identify the medical device 104 that the patient computer 108 is connected to. While assigning and transferring the medical device name may make the use of the medical device 104 easier, it is not required for completion the device-to-account association process.

In an example embodiment, the data transfer component 152 transfers a patient computer name to the host computer 112 for association with the user account during the device-to-account association process. The patient computer name is a unique identifier for the patient computer 108 on which the data transfer component 152 was installed and includes IP address, full computer name, or the like. In an example embodiment, the data transfer component 152 captures the patient computer name by requesting it from the patient computer processor.

As shown in FIG. 2B, the host computer 112 further includes a data receipt 160, and an authentication token generator 156. The data receipt 160 receives the unique ID, the patient computer name, and, optionally, the medical device name from the data transfer component 152 during the device-to-account association process. As will be described below in further detail, the data receipt 160 transfers the unique ID, the computer name, and the medical device name to the patient data depository 164 for association with the user account.

The authentication token generator 156 generates an authentication token and transfers the authentication token to the data transfer component 152 and to the patient data depository 164. In an example embodiment, the authentication token is a randomly generated cryptographic key, although other forms of authentication are also contemplated. In another example embodiment, the authentication token does not include patient personal credentials, e.g., name, date of birth, address and the like.

As described below in further detail, the data transfer component 152 stores the authentication token and uses it to securely pass-thru transfer patient medical data between the medical device 104 and the host computer 112 without storing patient personal credentials, e.g., name, date of birth, address and the like, on the data transfer component 152 or on the patient computer 108. In an example embodiment, the data transfer component 152 uses the authentication token to transfer patient medical data between the data uploader 148 and the data receipt 160 without storing patient personal credentials, name, date of birth, address and the like, on the data transfer component 152 or on the patient computer 108. In the example embodiment, the data transfer component 152 includes the authentication token with patient medical data for transfer between the data uploader 148 and the data receipt 160.

The data receipt 160 receives patient medical data from the data transfer component 152 and transfers received data to the patient data depository 164 for association with the user account. The patient data depository 164 receives transfers of patient medical data and associates the received patient medical data with the existing user account. In an example embodiment, the patient data depository 164 receives transfer of blood glucose measurements from a diabetes patient. The patient data depository 164 analyzes the authentication token attached with the received patient medical data. If the authentication token is associated with a user account then the patient data depository 164 retrieves the associated user account and associates the received patient medical data with the user account. In the example embodiment, therefore, the use of the authentication token enables patient medical data transfer without the user inputting their login credentials, i.e., user ID and password. In an alternative embodiment, the user 120 inputs their login credentials to enable the patient data depository 164 to associate the received patient medical data with the user account.

Referring to FIG. 2C, the data transfer component 152 includes a DTC-to-device interface 152-1, a DTC-to-device communication 152-2, a DTC-to-host interface 152-3, and a local store 168. The data transfer component 152 receives patient medical data from the data uploader 148 via the DTC-to-device interface 152-1. The data transfer component 152 transfers patient medical data to the data receipt 160 via the DTC-to-host interface 152-3. As will be described in more detail in reference to FIG. 4, the DTC-to-device interface 152-1 and the DTC-to-host interface 152-3 interact via DTC-to-device communication 152-2 to transfer patient medical data between the medical device 104 and the host computer 112. In an example embodiment, the local store 168 is a cache or a memory of the data transfer component 152. The local store 168 stores the unique ID of the medical device 104, the authentication token received from the authentication token generator 156, the patient computer name, and DTC configuration settings. In an example embodiment, the authentication token is a randomly generated cryptographic key and does not include patient personal credentials, e.g., name, date of birth, address, and the like. The data transfer component 152 attaches the authentication token along with patient medical data to securely pass-thru transfer patient medical data between the data uploader 148 and the data receipt 160. In the example embodiment, the configuration settings of the data transfer component 152 includes launch settings (e.g., launch automatically on the patient computer 108 startup), and the like.

Figure 3:
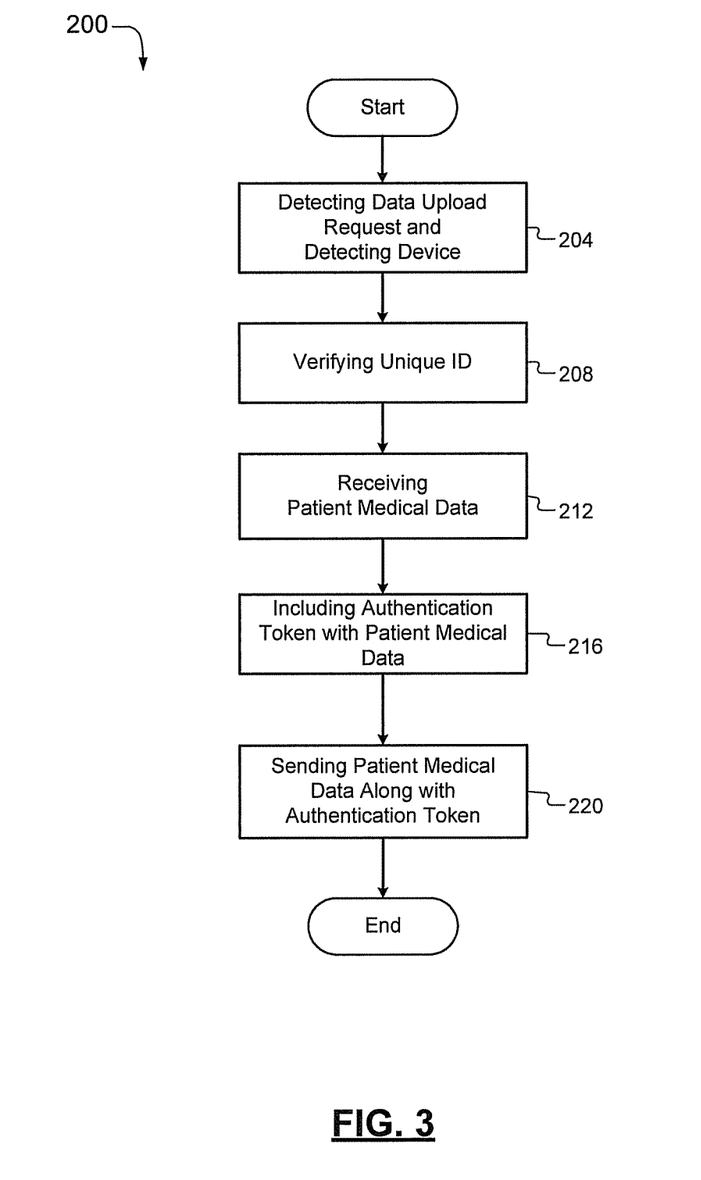
FIG. 3 is a flowchart illustrating a process that a data transfer component performs in order to transfer medical data.

FIG. 3 illustrates a flowchart of a method 200 for transferring medical data from the medical device 104 to the host computer 112 using the data transfer component 152. The transfer method 200 begins at 204, where the data transfer component 152 detects a data upload request and detects the medical device 104 ready to communicate. The data transfer component 152 verifies a unique ID at 208. If the unique ID is confirmed, the data transfer component 152 receives patient medical data, at 212. At 216, the data transfer component 152 attaches the authentication token with the patient medical data. In an example embodiment, the authentication token is cryptographic key and does not include patient personal credentials, e.g., name, date of birth, address and the like. The data transfer component 152 transfers the patient medical data along with the authentication token to the host computer 112, at 220. The transfer method 200 may then end. While the transfer method is shown as ending after 220, FIG. 3 is illustrative of one method iteration, and method may return to 204. The transfer method may be performed at a predetermined rate.

Figure 4:
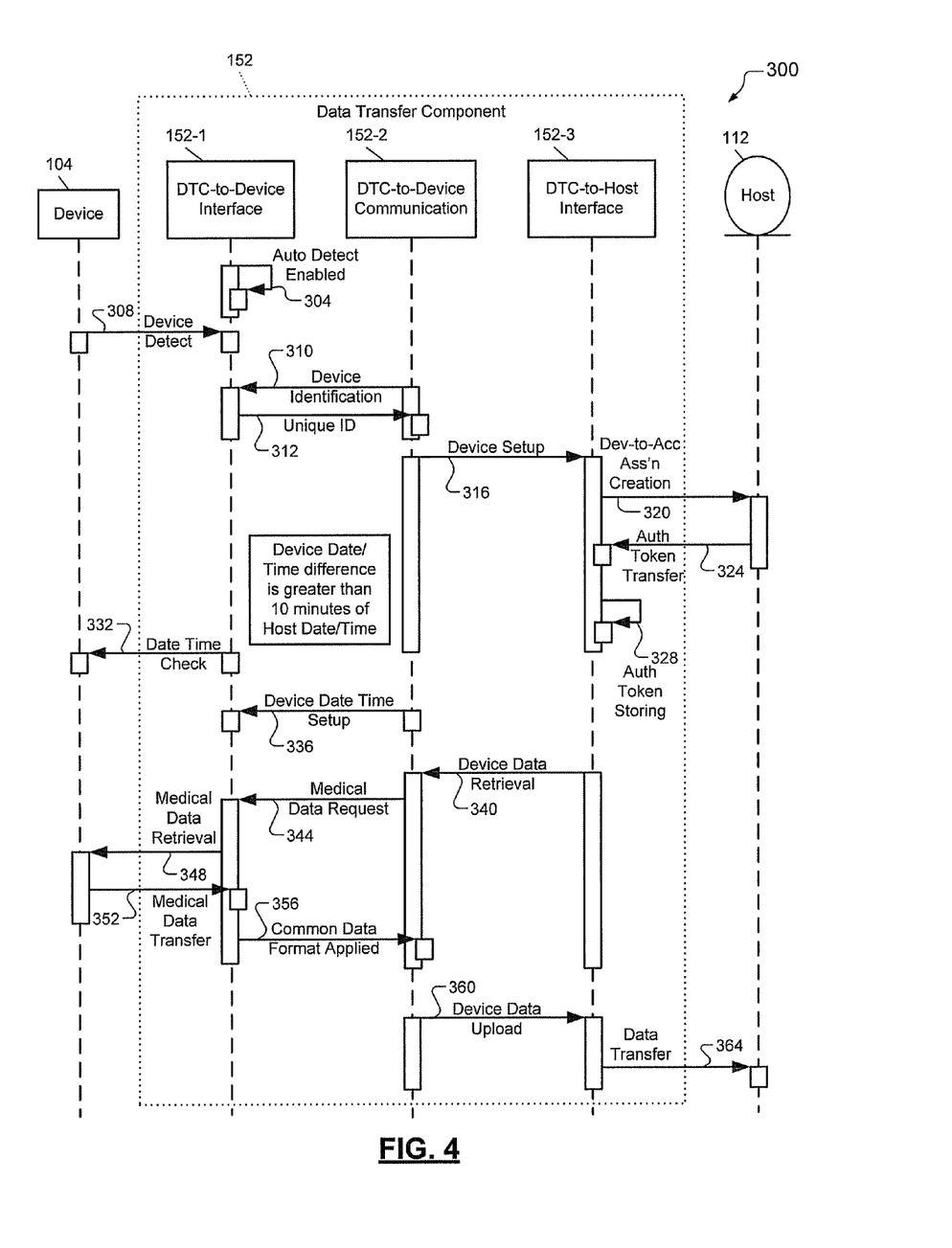
FIG. 4 is a sequence diagram of a device setup and data transfer using a data transfer component.

FIG. 4 is a sequence diagram illustrating an automatic upload process 300 used to transfer patient medical information between the medical device 104 and the host computer 112. The DTC-to-device interface 152-1 operates in an auto-detect mode or a manual mode. The auto-detect and manual modes may be mutually exclusive. The operation of the DTC-to-device interface 152-1 in the manual mode is described below in reference to FIG. 5. In an example embodiment, the DTC-to-device interface 152-1 in the auto-detect mode may use a network card antenna, e.g., Bluetooth, of the patient computer 108 to detect nearby devices available for communication. In an alternative embodiment, the DTC-to-device interface 152-1 monitors a USB port of the patient computer 108 to detect a connection of the medical device 104. In the example embodiment, the data transfer component 152 performs the automatic upload process when the auto-detect mode is enabled, at 304, and the DTC-to-device interface 152-1 detects the medical device 104, as shown at 308. Once the medical device 104 is detected, the DTC-to-device communication 152-2 requests the unique ID of the medical device 104, at 310. The DTC-to-device communication 152-2 then confirms, at 312, that the unique ID sent by the medical device 104 matches the unique ID stored in the local store 168.

If this is the first time the data transfer component 152 has been launched on the patient computer 108 following the installation process the host computer 112 may require further steps to complete a device-to-account association process. In an example embodiment, the DTC-to-device communication 152-2 sends device setup information, e.g., unique ID, patient computer name, medical device name, or the like, to the DTC-to-host interface 152-3, at 316. The host computer 112 creates the device-to-account association, at 320. In the example embodiment, the authentication token generator 156 generates the authentication token and associates it with the patient account. At 324, the authentication token generator 156 transfers the authentication token to the data transfer component 152 via the DTC-to-host interface 152-3. The data transfer component 152 stores the authentication token in the local store 168, at 328. In an example embodiment, the user 120 is not required to enter login credentials, e.g., user name and password, following completion of the device-to-account association process. In the example embodiment, the data transfer component 152 transfers data without requiring patient to enter their login credentials following completion of the device-to-account association process. In an alternative embodiment, the user 120 enters login credentials following completion of the device-to-account association process. In the alternative embodiment, the data transfer component 152 transfers data to the host computer 112 after the user 120 enters login credentials.

In some embodiments, the data transfer component 152 synchronizes date/time between the medical device 104 and the host computer 112. In an example embodiment, the DTC-to-device interface 152-1 performs a device date and time set check, at 332, and the DTC-to-device communication 152-2 performs the device date and time setup, at 336. The DTC-to-device communication 152-2 performs the device date and time setup if the DTC-to-device interface 152-1 finds that the device date/time and the host date/time differ by more than 10 minutes. In some other embodiments, the user 120 may elect to ignore date/time difference between the medical device 104 and the host computer 112.

The DTC-to-host interface 152-3 initiates a device data retrieval process, at 340. The DTC-to-device communication 152-2 then sends a medical data request, at 344, and the DTC-to-device interface 152-1 performs patient medical data retrieval, at 348. The medical device 104 transfers patient medical data, at 352, and the DTC-to-device interface 152-1 converts patient medical data to a common data format, at 356. In an example embodiment, the common data format is an XML-based data format defined for the host computer 112. The DTC-to-device communication 152-2 then attaches the authentication token along with converted data and uploads converted data to the DTC-to-host interface 152-3, at 360. The DTC-to-host interface 152-3 transfers converted data along with the authentication token to the host computer 112, at 364. In the example embodiment, the data receipt 160 of the host computer 112 receives converted data from the data transfer component 152 and transfers it to the patient data depository 164 for association with the user account. The data transfer component 152 transfers patient medical data to the data receipt 160 without storing patient personal credentials, name, date of birth, address and the like, on the local store 168 of the data transfer component 152 or on the patient computer 108. The patient data depository 164 analyzes the authentication token attached with the received patient medical data. If the authentication token is associated with a user account then the patient data depository 164 retrieves the associated user account and associates the received patient medical data with the user account.

Figure 5:
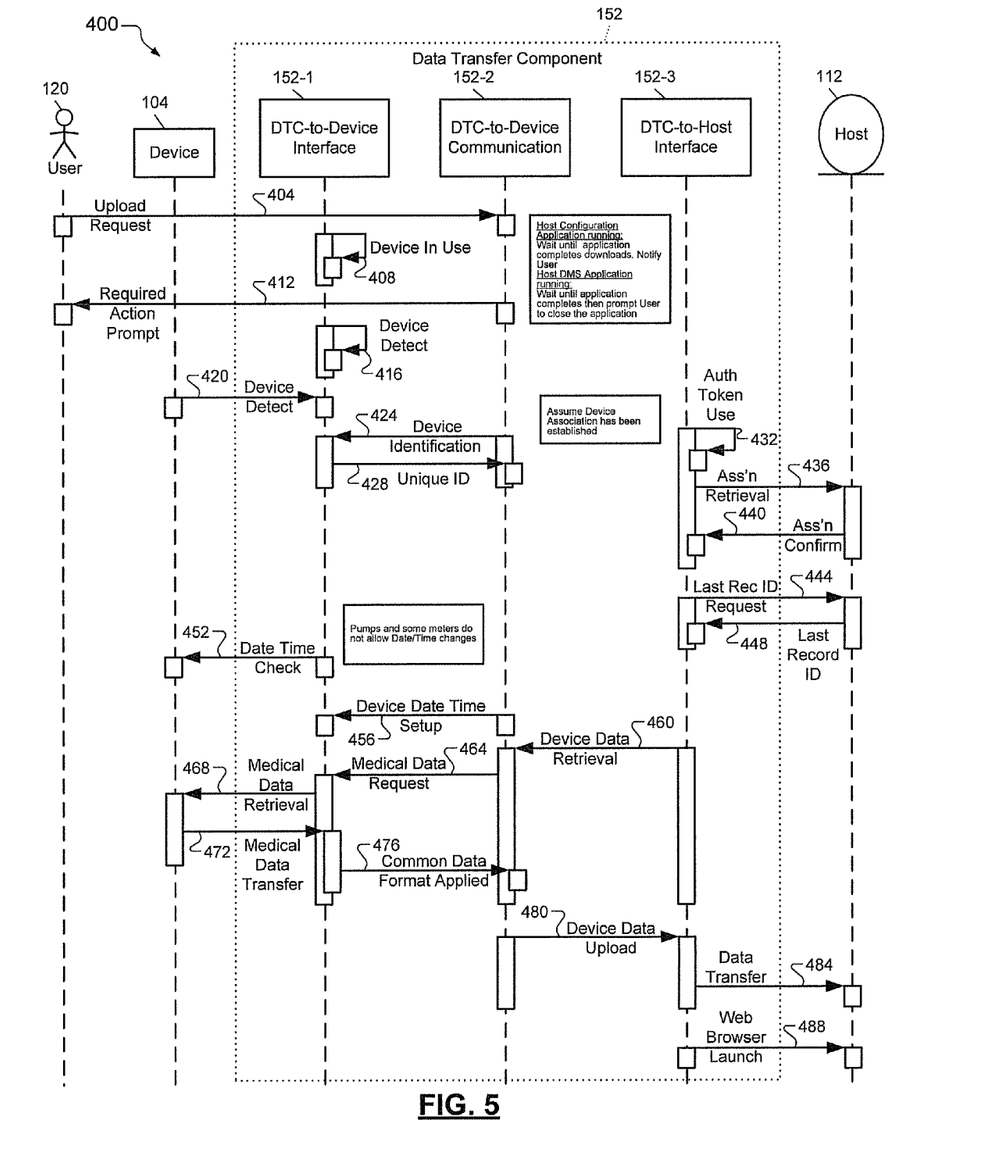
FIG. 5 is a sequence diagram of data transfer using a data transfer component based on an upload request.

FIG. 5 is a sequence diagram illustrating a manual upload process 400 used to transfer patient medical data between the medical device 104 and the host computer 112. To initiate the manual upload process 400, the user 120 sends an upload request to the DTC-to-device communication 152-2, at 404. In an example embodiment, the user 120 may select "Upload Medical Data" option from a user interface navigation menu. The DTC-to-device interface 152-1 confirms that the medical device 104 is ready to connect, at 408. The DTC-to-device interface 152-1 monitors a consolidated software connectivity library (CCL) to determine that the medical device 104 is not in use by another process and is ready to connect. If the medical device 104 is not ready to connect, the DTC-to-device 152-2 prompts the user 120 with required action, at 412.

The DTC-to-device interface 152-1 activates a device-detect process, at 416, and continually scans for devices available to communicate. The DTC-to-device interface 152-1 detects the medical device 104, at 420, and initiates data upload process. Once the medical device 104 is detected, the DTC-to-device communication 152-2 requests the unique ID from the medical device 104, at 424. The DTC-to-device communication 152-2 then confirms, at 428, that the unique ID received from the medical device 104 matches the unique ID stored in the local store 168.

In an example embodiment, if the device-to-account association already exists at the host computer 112 the DTC-to-host interface 152-3 requests confirmation of the authentication token associated with the medical device 104, at 432. The host computer 112 retrieves the authentication token associated with the medical device 104, at 436, and sends a confirmation to the DTC-to-host interface 152-3 that the authentication token is associated with the medical device 104, at 440. Alternatively, if the device-to-account association does not exist at the host computer 112, the authentication token generator 156 of the host computer 112 generates an authentication token and transfers the authentication token to the DTC-to-host interface 152-3, as described above in reference to FIG. 4, at 316-328.

In the example embodiment, the DTC-to-host interface 152-3 requests from the host computer 112 a last record ID, at 444, and the host computer responds with the last record ID, at 448. The last record ID is a data string identifying date of last patient medical data download based on the unique ID of the medical device 104.

As described previously in reference to FIG. 4, the data transfer component 152 may synchronize date/time between the medical device 104 and the host computer 112. In an example embodiment, the DTC-to-device interface 152-1 may then perform a device date and time set check, at 452, and the DTC-to-device communication 152-2 may perform the device date and time setup, at 456. In an alternative embodiment, medical devices, e.g., pumps and meters, do not allow date/time changes.

Similarly to the description in reference to FIG. 4, the data transfer component 152 transfers patient medical data between the medical device 104 and the host computer 112, at 460-484. In an example embodiment, the data receipt 160 of the host computer 112 receives converted data from the data transfer component 152 and transfers it to the patient data depository 164 for association with the user account. In the example embodiment, the data transfer component 152 transfers patient medical data to the data receipt 160 without storing patient personal credentials, name, date of birth, address and the like, on the local store 168 of the data transfer component 152 or on the patient computer 108. The patient data depository 164 analyzes the authentication token attached with the received patient medical data. If the authentication token is associated with a user account then the patient data depository 164 retrieves the associated user account and associates the received patient medical data with the user account. Following the transfer of patient medical data, the DTC-to-host interface 152-3 may send a web browser launch request to the host computer 112, at 488.

Figure 6:
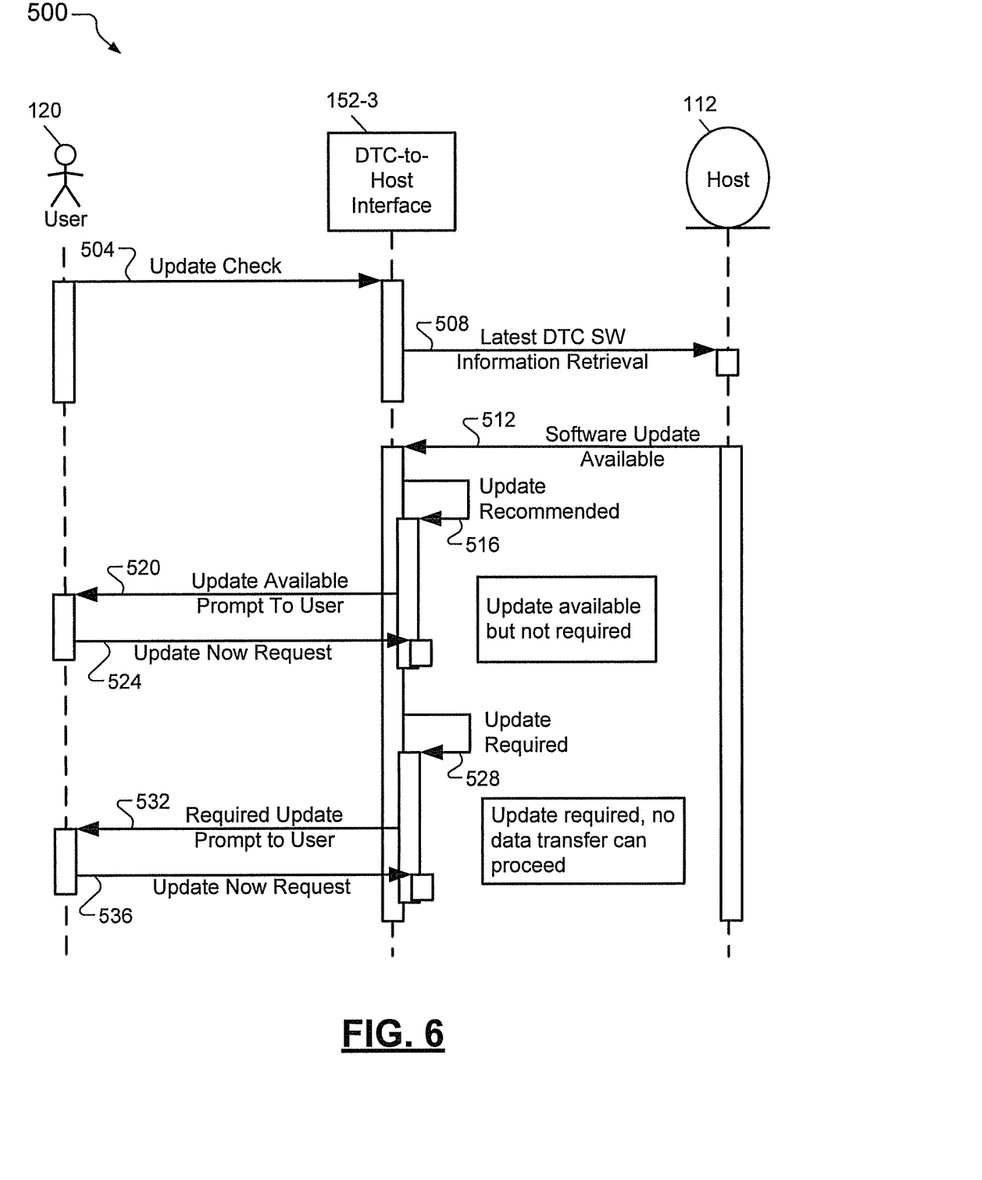
FIG. 6 is a sequence diagram of device update using a data transfer component based on a device update request.

FIG. 6 is a sequence diagram illustrating an update check process 500 used to perform software updates of the data transfer component 152. The user 120 invokes a check for updates on the patient computer 108 and initiates the update check process 500, at 504. In an example embodiment, the user 120 may select "Check for Updates" option using a web-based user interface via the patient computer 108. The DTC-to-host interface 152-3 sends a latest client software information retrieval request to the host computer 112, at 508. The host computer 112 responds indicating that a software update is available, at 512. The software update available may be a recommended update, i.e., patient medical data transfer can proceed without running the data transfer component 152 update. The software update available may instead be a required update, i.e., patient medical data transfer cannot proceed until the data transfer component 152 is updated.

In one instance, the DTC-to-host interface 152-3 detects that a recommended update is available for the data transfer device 152, at 516. The DTC-to-host interface 152-3 prompts the user 120 that the recommended update is available, at 520, and the user 120 responds requesting the recommended update, at 524. In the alternative, the DTC-to-host interface 152-3 detects that a required update is available for the data transfer device 152, at 528. The DTC-to-host interface 152-3 prompts the user 120 that the required update is available, at 532, and the user 120 responds requesting the required update, at 536.

In the alternative, the data transfer component 152 periodically checks for software update availability. Where the data transfer component 152 detects during periodical check for software update that the available software update is recommended, the data transfer component 152 prompts the user 120 that patient medical data transfer can proceed without updating the data transfer component 152. On the other hand, where the data transfer component 152 detects during periodical check for software update that the available software update is required, the data transfer component 152 prompts the user 120 that patient medical data transfer cannot proceed until the data transfer component 152 is updated.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented method for transferring medical data from a handheld medical recording device to a host computer, comprising:
   accessing, by a patient computer, a patient account using a web browser, where the account resides on the host computer and is associated with a patient;
   by the patient computer, downloading a device transfer component from the host computer via network;
   installing the device transfer component on the patient computer;
   when the device transfer component is launched for a first time after installation, by the device transfer component:

accessing the patient account residing at the host computer;
receiving a unique identifier of the handheld medical recording device from the handheld medical recording device;
storing the unique identifier of the handheld medical recording device in memory of the patient computer; and
transmitting the unique identifier of the handheld medical recording device to the host computer;
establishing, at the host computer, an association between the patient account and the unique identifier of the handheld medical recording device;
receiving, by the device transfer component, an authentication token from the host computer;
receiving, by the device transfer component from the handheld medical recording device, blood glucose (bG) measurements and the unique identifier of the handheld medical recording device;
determining, by the device transfer component, whether the unique identifier of the handheld medical recording device received with the bG measurements matches the unique identifier of the handheld medical recording device stored in the memory of the patient computer;
in response to determining that the unique identifier of the handheld medical recording device received with the bG measurements matches the unique identifier of the handheld medical recording device stored in the memory of the patient computer, passing, by the device transfer component, the bG measurements, along with the authentication token, to the host computer over the network; and
in response to determining that the authentication token is associated with the patient account, associating, at the host computer, the bG measurements with the patient account, where the association is made using the authentication token received with the bG measurements.

2. The computer-implemented method of claim 1 wherein the unique identifier of the handheld medical recording device includes at least one of a serial number and a model number of the handheld medical recording device.

3. The computer-implemented method of claim 1 further comprising, by the device transfer component, detecting that the handheld medical recording device is active before receiving the bG measurements from the handheld medical recording device.

4. The computer-implemented method of claim 1 further comprising, by the host computer, associating the bG measurements with the patient account without user input credentials,
wherein the credentials comprise a user name and a password used to access the patient account.

5. The computer-implemented method of claim 1, wherein the authentication token is a cryptographic key.

6. A computer-implemented method for transferring medical data from a handheld medical recording device to a host computer, comprising:
from the handheld medical recording device, receiving, by a device transfer component executed by a patient computer, a unique identifier of the handheld medical recording device;
storing, by the device transfer component, the unique identifier of the handheld medical recording device in memory of the patient computer;
transmitting, by the device transfer component, the unique identifier of the handheld medical recording device to the host computer;
establishing, at the host computer, an association between a patient account and the unique identifier of the handheld medical recording device;
receiving, by the device transfer component, an authentication token from the host computer;
receiving, by the device transfer component from the handheld medical recording device, bG measurements and the unique identifier of the handheld medical recording device; and
in response to determining that the unique identifier of the handheld medical recording device received with the bG measurements matches the unique identifier of the handheld medical recording device stored in the memory of the patient computer, passing, by the device transfer component to the host computer over the network, the bG measurements and the authentication token.

7. The computer-implemented method of claim 6 further comprising, by the device transfer component, detecting that the handheld medical recording device is active before receiving the bG measurements from the handheld medical recording device.

8. The computer-implemented method of claim 6 wherein the unique identifier includes at least one of a serial number and a model number of the handheld medical recording device.

9. The computer-implemented method of claim 6 wherein the authentication token is a cryptographic key.

10. The computer-implemented method of claim 6 further comprising, by the device transfer component, synchronizing first a date and time of the handheld medical recording device with a second date and time of the host computer.

11. The computer-implemented method of claim 1 further comprising, by the device transfer component, synchronizing first a date and time of the handheld medical recording device with a second date and time of the host computer.

* * * * *